US009468639B2

(12) United States Patent
Borsini et al.

(10) Patent No.: US 9,468,639 B2
(45) Date of Patent: *Oct. 18, 2016

(54) TREATING SEXUAL DESIRE DISORDERS WITH FLIBANSERIN

(71) Applicant: Sprout Pharmaceuticals, Inc., Raleigh, NC (US)

(72) Inventors: Franco Borsini, Bad Waldsee (DE); Kenneth Robert Evans, Toronto (CA)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,055

(22) Filed: Mar. 6, 2015

(65) Prior Publication Data

US 2015/0342948 A1 Dec. 3, 2015

Related U.S. Application Data

(63) Continuation of application No. 14/269,373, filed on May 5, 2014, now abandoned, which is a continuation of application No. 13/920,354, filed on Jun. 18, 2013, now abandoned, which is a continuation of application No. 13/551,036, filed on Jul. 17, 2012, now abandoned, which is a continuation of application No. 11/524,268, filed on Sep. 21, 2006, now Pat. No. 8,227,471, which is a continuation of application No. 10/272,603, filed on Oct. 16, 2002, now Pat. No. 7,151,103.

(60) Provisional application No. 60/348,911, filed on Oct. 23, 2001.

(30) Foreign Application Priority Data

Oct. 20, 2001 (EP) .................................... 01125020

(51) Int. Cl.
*A61K 31/496* (2006.01)

(52) U.S. Cl.
CPC .................................. *A61K 31/496* (2013.01)

(58) Field of Classification Search
CPC .................................................... A61K 31/496
See application file for complete search history.

(56) References Cited

U.S. PATENT DOCUMENTS

| | | | |
|---|---|---|---|
| 3,472,854 A | 10/1969 | Archer | |
| 4,438,091 A | 3/1984 | Gruber et al. | |
| 4,954,503 A | 9/1990 | Strupczewski et al. | |
| 5,281,585 A | 1/1994 | Duggan et al. | |
| 5,407,686 A | 4/1995 | Patel et al. | |
| 5,482,948 A | 1/1996 | Soyka et al. | |
| 5,576,290 A | 11/1996 | Hadley | |
| 5,576,318 A * | 11/1996 | Bietti .................... | C07D 235/26 514/252.19 |
| 5,883,094 A | 3/1999 | Fliri et al. | |
| 6,051,555 A | 4/2000 | Hadley | |
| 6,083,947 A * | 7/2000 | Granger ................. | A61K 31/00 514/249 |
| 6,281,218 B1 | 8/2001 | Cereda et al. | |
| 6,627,646 B2 | 9/2003 | Bakale et al. | |
| 7,151,103 B2 * | 12/2006 | Borsini ................ | A61K 31/496 514/252.19 |
| 7,183,410 B2 * | 2/2007 | Bombarda ........... | C07D 235/26 544/295 |
| 7,241,805 B2 | 7/2007 | Oberegger et al. | |
| 7,973,043 B2 | 7/2011 | Migaly | |
| 8,030,314 B2 | 10/2011 | Beck | |
| 8,227,471 B2 * | 7/2012 | Borsini ................ | A61K 31/496 514/254.06 |
| 8,545,886 B2 | 10/2013 | Eisenreich et al. | |
| 8,658,207 B2 | 2/2014 | Eisenreich et al. | |
| 8,722,682 B2 | 5/2014 | Volz et al. | |
| 8,785,458 B2 | 7/2014 | Ceci et al. | |
| 2002/0052370 A1 | 5/2002 | Barber et al. | |
| 2002/0091115 A1 | 7/2002 | Dyatkin et al. | |
| 2003/0055070 A1 | 3/2003 | Harrison et al. | |
| 2003/0083228 A1 | 5/2003 | Carpino et al. | |
| 2003/0104980 A1 | 6/2003 | Borsini et al. | |
| 2004/0048877 A1 | 3/2004 | Friedl et al. | |
| 2004/0147581 A1 | 7/2004 | Taylor et al. | |
| 2004/0198706 A1 | 10/2004 | Carrara et al. | |
| 2005/0090550 A1 | 4/2005 | Barrett | |
| 2005/0159430 A1 | 7/2005 | Bombarda et al. | |
| 2006/0252773 A1 | 11/2006 | Ceci | |
| 2006/0258640 A1 | 11/2006 | Ceci et al. | |
| 2007/0032654 A1 | 2/2007 | Bombarda et al. | |
| 2008/0069873 A1 | 3/2008 | Pearnchob et al. | |
| 2008/0103155 A1 | 5/2008 | Mendla et al. | |
| 2013/0172304 A1 | 7/2013 | Boeck | |
| 2013/0203671 A1 | 8/2013 | Castro et al. | |
| 2013/0203766 A1 | 8/2013 | Mendla et al. | |

FOREIGN PATENT DOCUMENTS

| | | |
|---|---|---|
| BE | 904945 A1 | 12/1986 |
| CA | 2 515 426 C | 1/2012 |
| EP | 0200322 A1 | 11/1986 |

(Continued)

OTHER PUBLICATIONS

Borsini et al., Behavioral Effects of Flibanserin (BIMT 17), Sep. 1999, Biochemistry and Behavior, vol. 64, Issue 1, pp. 137-146.
CMU Pharmaceutical Polymorphism, CMU Seed Fund Project on Detection and Control of Pharmaceutical Polymorphism, http://andrew.cmu.edu/user/suter/polymorph.html, as downloaded Apr. 3, 2008, 2002, pp. 1-3.
Bechard et al., Film Coating: Effect of Titanium Dioxide Concentration and Film Thickness on the Photostability of Nifedipine, International Journal of Pharmaceutics, 87 (1992), pp. 133-139.
U.S. Pharmacopia #23, 1995, pp. 1843-1844.

(Continued)

*Primary Examiner* — Trevor Love
(74) *Attorney, Agent, or Firm* — Additon, Higgins & Pendleton, P.A.

(57) ABSTRACT

The invention relates to the use of flibanserin, or a pharmaceutically acceptable acid addition salt thereof, for the treatment of disorders of sexual desire.

20 Claims, No Drawings

(56) References Cited

FOREIGN PATENT DOCUMENTS

| | | |
|---|---|---|
| EP | 0547517 A1 | 6/1993 |
| GB | 2023594 A | 1/1980 |
| JP | 58134033 | 8/1983 |
| WO | 98/19668 A1 | 5/1998 |
| WO | 99/64002 A1 | 12/1999 |
| WO | 00/64441 A2 | 11/2000 |
| WO | 02/72586 A1 | 9/2002 |
| WO | 02/74288 A2 | 9/2002 |
| WO | 03/13539 A1 | 2/2003 |
| WO | 03/030869 A | 4/2003 |
| WO | 2005/087207 A1 | 9/2005 |
| WO | 2006/019715 A1 | 2/2006 |
| WO | 2006/024471 A1 | 3/2006 |

OTHER PUBLICATIONS

Borsini et al., Pharmacology of Flibanserin, 2002, CNS Drug Reviews, vol. 8, No. 2, pp. 117-142, 26 pages.
Taavoni et al.; Psychogeriatrics, Hormone Replacement Therapy: Post-Menopausal Sex Life and Attitudes Towards Sex, 2005; 5:9-14, 6 pages.
Selective Serotonin Reuptake Inhibitors (SSRIs) Information; http://www.fda.gov/Drugs/DrugSafety/InformationbyDrugClass/ucm283587.htm as downloaded on Feb. 16, 2016; 2 pages.
Kurtel et al.; Journal of the American Society of Hypertension, Impaired Vasomotor Function Induced by the combination of Hypertension and Hypercholesterolemia, 2013; 7(1) pp. 14-23,10 pages.
Menopause Practice: A Clinician's Guide 3rd edition (NAMS 2007), 7 pages.
Katz et al.; Journal of Sex and Marital Therapy, the Relationship between Worry, Sexual Aversion, and Low Sexual Desire, 1999, vol. 25, Issue 4, abstract, 9 pages.
Office Action in European Patent Office in EP 09709701.8 on Oct. 22, 2015.
Kibbe et al.; Hydroxypropyl Methylcellulose: Handbook of Pharmaceutical Excipients, 2000, 6 pages, XP-002376679.
Office Action in counterpart European Patent Application No. 07728833.0; dated Aug. 21, 2012, 5 pages.
Office Action in counterpart European Patent Application No. 06764270.2; dated Mar. 6, 2012, 4 pages.
Office Action in counterpart Australian Patent Application No. 2006311038; dated Aug. 25, 2011, 2pages.
Office Action in counterpart Australian Patent Application No. 2007247094; dated Aug. 30, 2011, 2 pages.
Office action in counterpart Brazilian Patent Application No. PI0311189-0; dated Jun. 26, 2012, 10 pages.
Office Action in counterpart European Patent Application No. 07787338.8; dated Jul. 6, 2012, 4 pages.
Office Action in commonly owned Brazilian Patent Application No. PI0213358-0; dated Jul. 24, 2015, 4 pages.
Sexual and Gender Identity Disorders, Diagnostic and Statistical Manual of Mental Disorders, Fourth Edition Text Revision, American Psychiatric Association, 2000, 34 pages, 535-566.
Katz et al.; Efficacy of Flibanserin in Women with Hypoactive Sexual Desire Disorder: Results from the BEGONIA Trial; J Sex Med 2013, 10, 9 pages 1807-1815.
Singhal et al., Drug Polymorphism and Dosage Form Design: A Practical Perspective, Advanced Drug Delivery Reviews, 2004, 56 pages 335-347.
Otsuka et al., Effect of Polymorphic Forms of Bulk Powders on Pharmaceutical Properties of Carbamazepine Granules, Chem. Pharm. Bull., 1999, 47(6) pp. 852-856.
Gould, Salt selection for basic drugs, International Journal of Pharmaceutics vol. 33, Issues 1-3, Nov. 1986, pp. 201-217.
Giron et al: "Thermal analysis and calorimetric methods in the characterization of polymorphs and solvates" Thermochimica Acta, Elsevier Science Publishers, Amsterdam, NL, vol. 248, 1995, pp. 1-59.

Thrombolytic Therapy: MedlinePlus Medical Encyclopedia, http://www.nim.nih.gov/medlineplus/ency/article/007089.htm, accessed Sep. 17, 2015, pp. 1-5.
Walsh et al.; Sexual Dysfunction in the Older Woman, An Overview of the Current Understanding and Management; Drugs Aging 2004; 21 (10); pp. 656-675.
International Search Report for PCT/IB04/02286 mailed Sep. 24, 2004.
Semkova et al., Neuroprotective effect of 5-HT1A receptor agonist, Bay x 3702, demonstrated in vitro and in vivo, 1998, European Journal of Pharmacology, vol. 359, pp. 251-260.
Office Action in commonly owned Brazilian Patent Application No. 122012029907-3; dated Mar. 24, 2015, 11 pages.
Elger et al., Oedema reduction by levemopamil in focal cerebral ischemia of spontaneously hypertensive rats studied by magnetic resonance imaging, 1994, European Journal of Pharmacology, vol. 254, pp. 65-71.
Borsini et al., BIMT 17: a putative antidepressant with a fast onset of action?, 1997, Psychopharmacology, vol. 134, pp. 378-386.
Office Action in counterpart Canadian Patent Application No. 2,617,546; dated Mar. 25, 2013, 2 pages.
Vippagunta, et al., Advanced Drug Delivery Reviews, 2001; 48:3-26.
Office Action in counterpart Canadian Patent Application No. 2,626,134; dated Aug. 24, 2012, 2 pages.
Office Action in counterpart Canadian Patent Application No. 2,626,797; dated Aug. 21, 2012, 3 pages.
Poster, presented Nov. 6, 2009 at Sexual Medicine Society of North American 2009 Fall Scientific Meeting, 3 pages.
Transcript of Poster, presented Nov. 6, 2009 at Sexual Medicine Society of North American 2009 Fall Scientific Meeting, "Pooled Clinical Trial Analysis of Flibanserin Safety and Tolerability in Premenopausal Women with Hypoactive Sexual Desire Disorder", 7 pages.
Office Action in commonly owned Canadian Patent Application No. 2,649,938; dated Jan. 10, 2014, 3 pages.
Office Action in commonly owned Canadian Patent Application No. 2,654,798; dated Jan. 23, 2014, 2 pages.
Office Action in commonly owned Canadian Patent Application No. 2,617,546; dated Jul. 26, 2012, 2 pages.
Borsini F et al.: "BIMT 17, A 5-HT2A Receptor Antagonist and 5-HT1A Receptor Full Agonist in RAT Cerebral Cortex" Naunyn-Schmiedeberg's Archives of Pharmacology, Springer, Berlin, DE, vol. 352, No. 3, Sep. 1995, 7 pages 276-282.
Office Action in commonly owned Japanese Patent Application No. 2005-530787; dated Jun. 30, 2014, 2 pages.
Office Action in commonly owned European Patent Application No. 07728833.0; dated Apr. 9, 2013, 1 page.
Office Action in commonly owned Korean Patent Application No. 10-2008-7013699; dated Mar. 21, 2014, 5 pages.
Office Action in commonly owned Brazilian Patent Application No. PI0211601-4; dated Feb. 27, 2012 8 pages.
Office Action in commonly owned Chinese Patent Application No. 201310074677.5; dated Dec. 5, 2014, 8 pages.
Office Action in commonly owned European Patent Application No. 06807537.3; dated Mar. 8, 2013, 3 pages.
Office Action in commonly owned Canadian Patent Application No. 2,649,938; dated May 7, 2013, 3 pages.
Office Action in commonly owned Canadian Patent Application No. 2,654,798; dated May 7, 2013, 2 pages.
Office Action in commonly owned Canadian Patent Application No. 2,672,957; dated Nov. 1, 2013, 2 pages.
Office Action in counterpart Canadian Patent Application No. 2,563,743; dated Aug. 8, 2012, 2 pages.
Office Action in commonly owned Canadian Patent Application No. 2,802,600; dated Nov. 28, 2013, 2 pages.
Office Action in commonly owned Canadian Patent Application No. 2,682,015; dated Aug. 26, 2014, 2 pages.
Office Action in commonly owned Canadian Patent Application No. 2,802,600; dated Sep. 25, 2014, 2 pages.
New Collegiate Dictionary, 1981, p. 311 (i.e. definition of the term "diagnosis" as provided).

(56) References Cited

OTHER PUBLICATIONS

Office Action in commonly owned Korean Patent Application No. 10-2013-7033147; dated Feb. 28, 2014, 7 pages.
Office Action in commonly owned Chinese Patent Application No. 201310074677.5; dated Mar. 24, 2014, 8 pages.
Dennerstein et al.; Hypoactive Sexual Desire Disorder in Menopausal Women: A Survey of Western European Vomen; Journal of Sexual Medicine 2006; No. 3, 11 pages.
Leiblum et al.; Hypoactive Sexual Desire Disorder in Postmenopausal Women: US Results from the Women's International Study of Health and Sexuality (WISHeS); Menopause: The Journal of the North American Menopause Society 2006; vol. 13, No. 1, 11 pages.
Simon et al.; Efficacy and Safety of Flibanserin in Postmenopausal Women with Hypoactive Sexual Desire Disorder: Results of the Snowdrop Trial; Menopause: The Journal of the North American Menopause Society 2013; vol. 21, No. 6, 8 pages.
Office Action in commonly owned Canadian Patent Application No. 2,699,414; dated Oct. 30, 2014, 3 pages.
Crenshaw; The Sexual Aversion Syndrome; J. Sex Marital Ther.; 1985; vol. 11, Issue 4, abstract; 1 page.
Muir et al.; Dose Optimization of Intravenous Magnesium Sulfate After Acute Stroke; Stroke; May 1998; 29:918-923; 7 pages.
Khaled; Role of 5-HT Receptors in Treatment of Overactive Bladder; Drugs Today (Barc). Aug. 2003; 39 (8); 599-607 (abstract only); 2 pages.
Invernizzi; Flibanserin, a Potential Antidepressant Drug, Lowers 5-HT and Raises Dopamine and Noradrenaline in the Rat Prefrontal Cortex Dialysate: Role of 5-HT1A Receptors; British Journal of Pharmacology (2003) 39, 1281-1288; 3 pages.
Nitti; Duloxetine: A New Pharmacologic Therapy for Stress Urinary Incontinence; Reviews in Urology; 2004; vol. 6 (Suppl. 3): S48-S55; 8 pages.
Rezakhaniha; Efficacy of Desmopressin in Treatment of Nocturia in Elderly Men; J Res Med Sci.; Apr. 2011; 16 (4): 516-523; 8 pages.
Mayo Clinic: Overactive Bladder, 2015; http://www.mayoclinic.org/diseases-conditions/overactive-bladder/basics/ prevention/con-2; 3 pages.
Urinary Incontinence—Prevention—NHS Choices, 2014, http://www.nhs.uk/Conditions/Incontinence-urinary/Pages/Prevention.aspx.
Borsini et al.; Flibanserin: Antidepressant, 5-HT(1A) Receptor Agonist 5-HT2 Receptor Antagonist; Drugs of the Future; (1998) vol. 23, No. 1; pp. 9-16; 8 pages.
Dow; Using Dow Excipients for Controlled Release of Drugs in Hydrophilic Matrix Systems, 2006; pp. 1-34,36 pages.
Rueter et al.; Electrophysiological Examination of the Effects of Sustained Flibanserin Administration on Serotonin Receptors in Rat Brain; British Journal of Pharmacology 1999; 126, 627-638; 12 pages.
Steiner M: "Recogniffion of premenstrual dysphoric disorder and its treatment" Lancet The, Lancet Limited. London, GB, vol. 356, No. 9236, Sep. 30, 2000, pp. 1126-1127.
Office Action in commonly owned Canadian Patent Application No. 2,682,015; dated Dec. 20, 2013, 3 pages.
International Search Report for PCT/US00/18217 mailed Oct. 26, 2000.
International Search Report for PCT/EP00/08891 mailed Jan. 30, 2001.
International Search Report for PCT/US05/24623 mailed Nov. 4, 2005.
International Search Report for PCT/EP02/08466 mailed Nov. 21, 2002.
International Search Report for PCT/EP02/11103 mailed Jan. 14, 2003.
International Search Report for PCT/EP03/02184 mailed Aug. 12, 2003.
International Search Report for PCT/EP03/05226 mailed Sep. 17, 2003.
Borsini et al.; Further Characterization of Potential Antidepressant Action of Flibanserin; Psychopharmacology; (2001)159:64-69; 7 pages.
International Search Report for PCT/EP05/04081 mailed Oct. 11, 2005.
International Search Report for PCT/EP05/04086 mailed Oct. 11, 2005.
International Search Report for PCT/EP06/64825 mailed Nov. 17, 2006.
International Search Report for PCT/EP07/57064 mailed Nov. 6, 2007.
International Search Report for PCT/EP07/58301 mailed Jul. 24, 2008.
International Search Report for PCT/EP07/58302 mailed Jun. 4, 2008.
Office Action in counterpart Canadian Patent Application No. 2,563,743; dated Apr. 3, 2013, 2 pages.
Office Action in commonly owned Korean Patent Application No. 10-2008-7013699; dated Jun. 12, 2013, 10 pages.
Office Action in commonly owned Brazilian Patent Application No. PI0211601-4; dated Sep. 20, 2012, 9 pages.
Gao et al., "Efficacy and Safety of Flibanserin in Women with Hypoactive Sexual Desire Disorder: A Systematic Review and Meta-Analysis", J Sex Med, 2015, vol. 12, pp. 2095-2104.
Robinson, et al., "First Pharmacological Therapy for Hypoactive Sexual Desire Disorder in Premenopausal Women: Flibanserin", Annals of Pharmacotherapy, 2016, vol. 50(2), pp. 125-132.
Jaspers et al., "Efficacy and Safety of Flibanserin for the Treatment of Hypoactive Sexual Desire Disorder in Women: A Systematic Review and Meta-analysis", Abstract downloaded at http://www.ncbi.nlm.nih.gov/pubmed/26927498 on May 19, 2016, pp. 1-2.

* cited by examiner

TREATING SEXUAL DESIRE DISORDERS WITH FLIBANSERIN

RELATED APPLICATIONS

This application is a continuation of U.S. patent application Ser. No. 14/269,373 for TREATING SEXUAL DESIRE DISORDERS WITH FLIBANSERIN; filed May 5, 2014, which is a continuation of U.S. patent application Ser. No. 13/920,354 for TREATING SEXUAL DESIRE DISORDERS WITH FLIBANSERIN, filed Jun. 18, 2013, which is a continuation of U.S. patent application Ser. No. 13/551,036 for TREATING SEXUAL DESIRE DISORDERS WITH FLIBANSERIN, filed Jul. 17, 2012, which is a continuation of U.S. patent application Ser. No. 11/524,268 for TREATING SEXUAL DESIRE DISORDERS WITH FLIBANSERIN, filed Sep. 21, 2006, now U.S. Pat. No. 8,227,471, which is a continuation of U.S. patent application Ser. No. 10/272,603, for METHOD OF TREATING FEMALE HYPOACTIVE SEXUAL DESIRE DISORDER WITH FLIBANSERIN, filed Oct. 16, 2002, now U.S. Pat. No. 7,151,103, which claims the benefit (i) of U.S. Provisional Patent Application Ser. No. 60/348,911 for SEXUAL DESIRE ENHANCING MEDICAMENTS, filed Oct. 23, 2001, and (ii) European Patent Application No. EP 01125020.6 for USE OF FLIBANSERIN IN THE TREATMENT OF SEXUAL DISORDERS, filed Oct. 20, 2001. This nonprovisional application claims the benefit of and incorporates entirely by reference these U.S. nonprovisional patent applications, U.S. provisional patent application, and European patent application.

FIELD OF THE INVENTION

The invention relates to the use of flibanserin for the preparation of a medicament for the treatment of disorders of sexual desire.

BACKGROUND OF THE INVENTION

The compound 1-[2-(4-(3-trifluoromethyl-phenyl)piperazin-1-yl)ethyl]-2,3-dihydro-1H-benzimidazol-2-one (flibanserin) is disclosed in form of its hydrochloride in European Patent Application EP-A-526434 and has the following chemical structure:

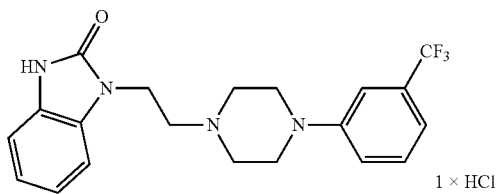 [SMILES: O=c1[nH]c2ccccc2n1CCN1CCN(c2cccc(C(F)(F)F)c2)CC1]

Flibanserin shows affinity for the 5-HT1A and 5-HT2-receptor. It is therefore a promising therapeutic agent for the treatment of a variety of diseases, for instance depression, schizophrenia, and anxiety.

DETAILED DESCRIPTION OF THE INVENTION

In studies of male and female patients suffering from sexual dysfunction it has been found that flibanserin optionally in form of the pharmacologically acceptable acid addition salts thereof displays sexual desire enhancing properties. Accordingly, the instant invention relates to the use of flibanserin, optionally in form of the pharmacologically acceptable acid addition salts thereof for the preparation of a medicament for the treatment of disorders of sexual desire.

In a preferred embodiment the invention relates to the use of flibanserin, optionally in form of the pharmacologically acceptable acid addition salts thereof for the preparation of a medicament for the treatment of disorders selected from the group consisting of Hypoactive Sexual Desire Disorder, loss of sexual desire, lack of sexual desire, decreased sexual desire, inhibited sexual desire, loss of libido, libido disturbance, and frigidity.

Particular preferred according to the invention is the use of flibanserin, optionally in form of the pharmacologically acceptable acid addition salts thereof for the preparation of a medicament for the treatment of disorders selected from the group consisting of Hypoactive Sexual Desire Disorder, loss of sexual desire, lack of sexual desire, decreased sexual desire, inhibited sexual desire.

In a particularly preferred embodiment the invention relates to the use of flibanserin, optionally in form of the pharmacologically acceptable acid addition salts thereof for the preparation of a medicament for the treatment of disorders selected from the group of Hypoactive Sexual Desire Disorder and loss of sexual desire.

The observed effects of flibanserin can be achieved in men and woman. However, according to a further aspect of the invention the use of flibanserin optionally in form of the pharmacologically acceptable acid addition salts thereof for the preparation of a medicament for the treatment of female sexual dysfunction is preferred.

The beneficial effects of flibanserin can be observed regardless of whether the disturbance existed lifelong or was acquired, and independent of etiologic origin (organic—both, physically and drug induced-, psychogen, a combination of organic—both, physically and drug induced-, and psychogen, or unknown).

Flibanserin can optionally used in form of its pharmaceutically acceptable acid addition salts. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred.

Flibanserin, optionally used in form of its pharmaceutically acceptable acid addition salts, may be incorporated into the conventional pharmaceutical preparation in solid, liquid or spray form. The composition may, for example, be presented in as form suitable for oral, rectal, parenteral administration or for nasal inhalation: preferred forms includes for example, capsules, tablets, coated tablets, ampoules, suppositories and nasal spray. The active ingredient may be incorporated in excipients or carriers conventionally used in pharmaceutical compositions such as, for example, talc, arabic gum, lactose, gelatine, magnesium stearate, corn starch, aqueous or non aqueous vehicles, polyvinyl pyrrolidone, semisynthetic glicerides of fatty acids, benzalconium chloride, sodium phosphate, EDTA, polysorbate 80. The compositions are advantageously formulated in dosage units, each dosage unit being adapted to supply a single dose of the active ingredient. The dosis range applicable per day is between 0.1 to 400, preferably between 1.0 to 300, more preferably between 2 to 200 mg.

Each dosage unit may conveniently contain from 0.01 mg to 100 mg, preferably from 0.1 to 50 mg.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the cure may also consist of as number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. of a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. of with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The Examples which follow illustrate the present invention without restricting its scope:

Examples of Pharmaceutical Formulations

A)

| Tablets | per tablet |
| --- | --- |
| flibanserin hydrochloride | 100 mg |
| lactose | 240 mg |
| corn starch | 340 mg |
| polyvinylpyrrolidone | 45 mg |
| magnesium stearate | 15 mg |
| | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn march and the magnesium stearate are screened and mixed together. The mixture is compressed to produce tablets of suitable shape and size.

B) Tablets Per Tablet

| | |
| --- | --- |
| flibanserin hydrochloride | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture it compressed to form tablets of a suitable size.

C)

| Coated tablets | per coated tablet |
| --- | --- |
| flibanserin hydrochloride | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are thoroughly mixed and moistened with water. The moist mass is pushed through is screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D)

| Capsules | per capsule |
| --- | --- |
| flibanserin hydrochloride | 1 50 mg |
| Corn starch | 268.5 mg |
| Magnesium stearate | 1.5 mg |
| | 420 mg |

The substance and corn starch are mixed and moistened with water. The moist mass is screened and dried. The dry granules are screened and mixed with magnesium stearate. The finished mixture is packed into size 1 hard gelatine capsules.

E) Ampoule Solution

| | |
| --- | --- |
| flibanserin hydrochloride | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and seated by fusion.

F) Suppositories

| flibanserin hydrochloride | 50 mg |
|---|---|
| solid fat | 1650 mg |
| | 1700 mg |

The hard fat is melted. At 40° C. the ground active substance is homogeneously dispersed. It is cooled to 38° C. and poured into slightly chilled suppository moulds.

The invention claimed is:

1. A method of treating decreased sexual desire in a patient, comprising administering a therapeutically effective amount of flibanserin or a pharmaceutically acceptable acid addition salt thereof to the patient to treat decreased sexual desire.

2. The method according to claim 1, wherein the patient is female.

3. The method according to claim 1, wherein the patient is male.

4. The method according to claim 1, wherein the amount administered is between about 0.1 mg and 400 mg per day of flibanserin or a pharmaceutically acceptable acid addition salt thereof.

5. The method according to claim 1, wherein the amount administered is between about 1 mg and 300 mg per day of flibanserin or a pharmaceutically acceptable acid addition salt thereof.

6. The method according to claim 1, wherein the amount administered is in a dosage unit containing between about 0.01 mg and 100 mg of flibanserin or a pharmaceutically acceptable acid addition salt thereof.

7. The method according to claim 1, wherein the amount administered is in a dosage unit containing between about 0.1 mg and 50 mg of flibanserin or a pharmaceutically acceptable acid addition salt thereof.

8. A method of treating absent sexual desire in a patient, comprising administering a therapeutically effective amount of flibanserin or a pharmaceutically acceptable acid addition salt thereof to the patient to treat decreased sexual desire.

9. The method according to claim 8, wherein the patient is female.

10. The method according to claim 8, wherein the patient is male.

11. The method according to claim 8, wherein the amount administered is between about 2 mg and 200 mg per day of flibanserin or a pharmaceutically acceptable acid addition salt thereof.

12. The method according to claim 8, wherein the amount administered is between about 0.1 mg and 100 mg per day of flibanserin or a pharmaceutically acceptable acid addition salt thereof.

13. The method according to claim 8, wherein the amount administered is in a dosage unit containing about 150 mg of flibanserin or a pharmaceutically acceptable acid addition salt thereof.

14. A method of treating inhibited sexual desire in a patient, comprising administering a therapeutically effective amount of flibanserin or a pharmaceutically acceptable acid addition salt thereof to the patient to treat decreased sexual desire.

15. The method according to claim 14, wherein the patient is female.

16. The method according to claim 14, wherein the patient is male.

17. The method according to claim 14, wherein the amount administered is between about 0.1 mg and 400 mg per day of flibanserin or a pharmaceutically acceptable acid addition salt thereof.

18. The method according to claim 14, wherein the amount administered is in a dosage unit containing about 100 mg of flibanserin or a pharmaceutically acceptable acid addition salt thereof.

19. The method according to claim 14, wherein the amount administered is in a dosage unit containing about 80 mg of flibanserin or a pharmaceutically acceptable acid addition salt thereof.

20. The method according to claim 14, wherein the amount administered is in a dosage unit containing about 50 mg of flibanserin or a pharmaceutically acceptable acid addition salt thereof.

* * * * *